(12) United States Patent
Klein Koerkamp et al.

(10) Patent No.: US 9,151,968 B2
(45) Date of Patent: Oct. 6, 2015

(54) INTEGRATED OPTICAL WAVEGUIDE INTERFEROMETRIC SENSOR

(75) Inventors: Hermanus Marcellinus Maria Klein Koerkamp, Enschede (NL); Tonnis Meindert Koster, Enschede (NL); Martinus Bernardus Johannes Diemeer, Limmen (NL)

(73) Assignee: Optisense B.V., Enschede (NL)

( * ) Notice: Subject to any disclaimer, the term of this patent is extended or adjusted under 35 U.S.C. 154(b) by 0 days.

(21) Appl. No.: 13/143,411

(22) PCT Filed: Jan. 22, 2010

(86) PCT No.: PCT/EP2010/050743
§ 371 (c)(1),
(2), (4) Date: Aug. 18, 2011

(87) PCT Pub. No.: WO2010/089209
PCT Pub. Date: Aug. 12, 2010

(65) Prior Publication Data
US 2011/0292398 A1 Dec. 1, 2011

(30) Foreign Application Priority Data

Feb. 3, 2009 (EP) .................................... 09151982

(51) Int. Cl.
*G02F 1/01* (2006.01)
*G01N 21/77* (2006.01)
(Continued)

(52) U.S. Cl.
CPC .......... *G02F 1/0147* (2013.01); *G01N 21/7703* (2013.01); *G01N 33/54373* (2013.01);
(Continued)

(58) Field of Classification Search
CPC ............... G01N 2021/458; G01N 2021/7779; G01N 21/7703; G01N 33/54373; G02F 1/0147
USPC .............................. 356/477, 481, 517, 70, 450
See application file for complete search history.

(56) References Cited

U.S. PATENT DOCUMENTS 4,940,328 A * 7/1990 Hartman ....................... 356/481
(Continued)

FOREIGN PATENT DOCUMENTS

EP 1918695 5/2008
(Continued)

OTHER PUBLICATIONS

RS Moshrefzadeh et al., "Temperature Dependence of Index of Refraction of Polymeric Waveguides", Apr. 1992, J. of Lightwave Tech., vol. 10, No. 4, pp. 420-425.*
(Continued)

*Primary Examiner* — Gregory J Toatley
*Assistant Examiner* — Hina F Ayub
(74) *Attorney, Agent, or Firm* — McDonnell Boehnen Hulbert & Berghoff LLP

(57) ABSTRACT

Integrated optical waveguide interferometer for evanescent sensing of chemical and/or physical quantities, comprising a substrate carrying a waveguide layer structure provided with: —a first waveguide core layer sandwiched between two first cladding layers formed by a first lower and a first upper (6) cladding layer, of a lower refractive index than the first waveguide core layer, —a second waveguide core layer sandwiched between two second claddings layers formed by a second lower and a second upper (6) cladding layer, of a lower refractive index than the second waveguide core layer, —a splitter (2) and a combiner (5) for optically coupling said first and second waveguide core layers at first and second junctions, respectively, characterized by —a modulation section of a polymer cladding material (9) included in one of the first upper cladding layers (6) and/or included in one of the second upper cladding layers (6), the polymer cladding material covering an identifiable area of said first waveguide core layer and/or said second waveguide core layer between the first and second junctions, said polymer cladding material having an index of refraction between 1.46 and 2.5 that varies with temperature, thereby changing the phase of radiation propagating through said first and second waveguide core layers, means (10) for raising and lowering the temperature of said polymer cladding material (9).

28 Claims, 3 Drawing Sheets

(51) Int. Cl.
*G01N 33/543* (2006.01)
*G01N 21/45* (2006.01)

(52) U.S. Cl.
CPC .. *G01N2021/458* (2013.01); *G01N 2021/7736* (2013.01); *G01N 2021/7779* (2013.01); *G02F 2202/022* (2013.01)

(56) References Cited

U.S. PATENT DOCUMENTS

| | | | |
|---|---|---|---|
| 5,583,637 A * | 12/1996 | Tokano et al. | 356/477 |
| 5,644,125 A * | 7/1997 | Wobschall | 250/227.27 |
| 6,240,226 B1 | 5/2001 | Presby et al. | |
| 6,385,383 B1 * | 5/2002 | Marcuse et al. | 385/140 |
| 6,429,023 B1 * | 8/2002 | Gharavi | 436/167 |
| 7,228,013 B1 * | 6/2007 | Bramson et al. | 385/3 |
| 2004/0158021 A1 * | 8/2004 | Sadayori et al. | 528/44 |
| 2004/0257579 A1 * | 12/2004 | Shirai et al. | 356/477 |
| 2004/0257635 A1 * | 12/2004 | Paolini et al. | 359/296 |
| 2006/0165340 A1 | 7/2006 | Wu | |
| 2007/0177151 A1 * | 8/2007 | Isomura et al. | 356/477 |
| 2008/0166095 A1 * | 7/2008 | Popovic et al. | 385/126 |
| 2010/0001268 A1 * | 1/2010 | Frye et al. | 257/48 |
| 2010/0271634 A1 * | 10/2010 | Dominguez Horna et al. | 356/477 |

FOREIGN PATENT DOCUMENTS

| | | |
|---|---|---|
| FR | 2774887 | 8/1999 |
| WO | WO2008/096296 | 8/2008 |

OTHER PUBLICATIONS

B. Sepulveda et al. "Magneto-optical phase modulation in integrated Mach-Zehnder interferometric sensors", Jul. 24, 2006, Sensors and Actuators A 134 (2007) pp. 339-347.*

International Search Report and Written Opinion, PCT International Application No. PCT/EP2010/050743 dated Mar. 23, 2010.

* cited by examiner

INTEGRATED OPTICAL WAVEGUIDE INTERFEROMETRIC SENSOR

CROSS REFERENCE TO RELATED APPLICATIONS

The present application is a national stage entry of PCT/EP2010/050743, filed Jan. 22, 2010, and claims priority to EP 09151982.7, filed Feb. 3, 2009, the entire contents of which is incorporated herein by reference.

The present invention relates to an integrated optical waveguide interferometer for evanescent sensing of chemical and/or physical quantities, comprising a substrate carrying a waveguide layer structure provided with a first waveguide core layer sandwiched between two first claddings layers formed by a first lower and a first upper cladding layer, of a lower refractive index than the first waveguide core layer, a second waveguide core layer sandwiched between two second claddings layers formed by a second lower and a second upper cladding layer, of a lower refractive index than the second waveguide core layer, a splitter and a combiner for optically coupling said first and second waveguide core layers at first and second junctions, respectively.

Such an integrated optical waveguide interferometer is known from U.S. Pat. No. 6,240,226 (Lucent Technologies, Inc.). The integrated optical waveguide interferometer described therein is of the Mach-Zehnder type. This known Mach-Zehnder interferometer includes a first waveguide core channel and a second waveguide core channel, both brought close together at a first directional coupler and a second directional coupler. The first waveguide core channel is surrounded at all sides not in contact with the substrate by a first cladding and the second waveguide core is surrounded at all sides not in contact with the substrate, by a second cladding. The first cladding includes a section of a polymer cladding in contact, at all sides not in contact with the substrate, with the first waveguide core channel between the first and the second directional couplers. Outside the polymer section, the first waveguide core channel is surrounded by a standard cladding material. The second waveguide core is similar to the first waveguide core except that a standard cladding material is employed throughout its length. The polymer cladding has an index of refraction that varies with temperature. The temperature of the section of polymer cladding is adjusted to cause a corresponding change in the phase of light flowing through the first waveguide core bounded by the polymer cladding to effect a desired switching or modulation of the light.

It is noted that the present invention is not limited to a Mach-Zehnder interferometer, but also extends to other interferometers, such as a so-called Michelson interferometer or a so-called Young interferometer. However, the present invention particularly relates to a so-called planar optical waveguide interferometer, that is an interferometer consisting of a thin transparent core film sandwiched between transparent cladding layers with lower refractive indices that confine the propagating light in the core film such that a large evanescent optical sensing field is present in the cladding layers, wherein such a waveguide stack is preferably deposited on a flat smooth substrate for the purpose of mechanical stability. Further, in the framework of the present invention the splitter and the combiner do not only refer to a first and a second directional coupler, as described in said U.S. Pat. No. 6,240,226, but also refer to, for example, a first micro-optic beam splitting cube and a second micro-optic beam splitting cube, or a first Y-branch splitter and a second Y-branch splitter, respectively. Finally, the term "evanescent sensing" as used above is a term well-known in the art, that is applying a chemically sensitive material as a cladding layer within a window obtained by locally removing the originally applied cladding layer.

A disadvantage of an integrated optical waveguide interferometer known from said U.S. Pat. No. 6,240,226 is that, dependent on the technical field of use, the efficiency and accuracy in sensing applications do not meet today's wishes. For sensing applications a large evanescent field is required, which forces the core to be thin and predominantly planar with no or only shallow ridge structuring. A polymer cladding section will therefore cover only the upper part of the waveguide core. Consequently, thermo-optic modulation will not be as efficient for a polymer cladding surrounding the core at all sides not in contact with the substrate.

Therefore, it is an objective of the invention to improve the prior art and to accomplish that objective with an interferometer of the type mentioned in the preamble according to the invention is characterized by a modulation section of a polymer cladding material included in one of the first upper cladding layers and/or included in one of the second upper cladding layers, the polymer cladding material covering an identifiable area of said first waveguide core layer and/or said second waveguide core layer between the first and second junctions, said polymer cladding material having an index of refraction between 1.46 and 2.5 that varies with temperature, thereby changing the phase of radiation propagating through said first and second waveguide core layers, means for raising and lowering the temperature of said polymer cladding material.

An important feature is thus that a modulation section is obtained by means of an asymmetric layer structure equipped with said section of polymer cladding material having a higher refractive index than the lower cladding layer, selected such that the evanescent field is close to "cut-off". This means that the evanescent field is pulled into said section of polymer cladding material, whereas thermal changes in its refractive index will have a strong effect on the effective refractive index of the structure.

Particularly, said interferometer according to the invention satisfies the equations in said modulation section:

$$n_c > n_s \quad (1)$$

$$V = 2\pi(h/\lambda)(n_f^2 - n_c^2)^{1/2} \quad (2)$$

$$r = (n_f^2 - n_s^2)/(n_f^2 - n_c^2) \quad (3)$$

with $n_c$ being the refractive index of the first upper cladding layer and/or the second upper cladding layer;

$n_s$ being the refractive index of the first lower cladding layer and/or the second lower cladding layer;

$n_f$ being the refractive index of the first core layer and/or the second core layer;

h being the thickness of the first core layer and/or the second core layer;

$\lambda$ being the optical wavelength;

V varying between 0.1 and 4 for r>1.1.

An important feature of a preferred embodiment of the present interferometer is an optimization of the thermo-optic efficiency (required power for a given effective index change) by a choice of the refractive index of the polymer cladding, $n_c$, such that the optical mode has a large evanescent field in that cladding. The conditions for that are as follows:

1) The refractive index of the polymer cladding, $n_c$, is close to that of the core $n_f$. This induces the cut-off of the mode with strong field expansion out of the core. A measure for this condition is the value of the so-called V-parameter: $V=2\pi(h/\lambda)(n_f^2-n_c^2)^{1/2}$ For a symmetric waveguide having a identical refractive index for the polymer upper cladding and the lower cladding the cut-off condition for the fundamental mode is at $V=0$. The first order mode can exist starting from $V=\pi$ (note that the waveguide should stay monomodal).

For a highly asymmetric waveguide, having a large refractive index difference between the polymer (upper) cladding and the lower cladding, n, the cut-off of the fundamental mode occurs at $V=\pi/2$. The first order mode can exists starting from $V=3\pi/2$.

2) The refractive index difference between the polymer upper cladding and the lower cladding, n, is large (high asymmetry). This induces the field expansion to occur exclusively in the polymer cladding. A quality measure for this condition is the ratio of the optical power at the boundaries of the core with the polymer cladding ($P_c$) and with lower cladding ($P_s$). For the TE modes this ratio, $P_c/P_s$, is: $P_c/P_s=r=(n_f^2-n_s^2)/(n_f^2-n_c^2)$ Therefore, a suitable choice for V would be in the range between $V=0.1$ and $V=4$ in combination with a value for r in the range of $r>1.1$.

Preferably, said polymer cladding material is at least substantially made from a material selected from the group consisting of poly pentabromophenyl methacrylate, poly pentabromophenyl acrylate, poly pentabromobenzyl methacrylate, poly pentabromobenzyl acrylate, poly 2,4,6-tribromophenyl methacrylate, polyvinylphenyl sulfide, poly 1-napthyl methacrylate, poly 2-vinylthiophene, poly 2,6-dichloro styrene, poly N-vinylphthalamide, and poly 2-chlorostyrene en poly pentachlorophenyl methacrylate. In the alternative, said polymer cladding material is at least substantially made from a material selected from the group consisting of a polymer based on aromatic benzene rings and a polymer based on fused aromatic rings, such as an SU-8 epoxy monomer or an aromatic polyimide. Preferably, high refractive index particles have been added to the material of said polymer cladding material in order to increase the index of refraction thereof.

Preferably said lower cladding layer is made from thermally grown or chemical vapor deposited (CVD) silica, silica containing multicomponent glasses, fluoride glasses, silicon containing organic polymers or silica containing hybrid organic-inorganic polymers or fluorine containing organic polymers or fluorine containing hybrid organic-inorganic polymers.

In one preferred embodiment of an integrated optical waveguide interferometer in accordance with the invention said means for raising and lowering the temperature of said polymer cladding material comprises a heater and/or a cooler adjacent to the section of said polymer cladding material. Said heater and/or cooler may include electrical resistive heater stripes or thermo-electric cooling/heating elements that are disposed near said polymer section(s).

In a further preferred embodiment of an integrated optical waveguide interferometer according to the invention said first waveguide core layer and/or said second waveguide core layer is/are provided with a profile in the form of a ridge.

In a further preferred embodiment of an integrated optical waveguide interferometer in accordance with the invention the refractive index of said first waveguide core layer and/or said second waveguide core layer is selected in the range between 1.5 and 2.5. Particularly, said first waveguide core layer and/or said second waveguide core layer is/are at least substantially made from a material selected from the group consisting of $Si_3N_4$, $TiO_2$, $Ta_2O_5$, $ZrO_2$, $Al_2O_3$, $Y_2O_3$ and $Nb_2O_5$.

In a further preferred embodiment of an integrated optical waveguide interferometer according to the invention a foam is applied on said means for raising and lowering the temperature of said polymer cladding material.

The present interferometer might be sensitive for air turbulences above the means for raising and lowering the temperature of said polymer cladding material, that is the heaters. These induce interfering signal fluctuations. This can be avoided by applying thin polyurethane (PUR) foam layers as thermal isolators on top of the heaters. PUR foam is an excellent thermal isolator. The foam layer can be applied by dripping a diluted PUR pre-polymer solution onto the heaters and allowing this to cure as a foam layer by moisture uptake from ambient atmosphere. Alternatively, the heaters can be covered with a coverplate of a more dense material, while leaving a narrow, thermally isolating air gap between the surface of the heaters and the coverplate.

In a further preferred embodiment of an integrated optical waveguide interferometer in accordance with this invention means are provided for electrical modulation of a signal of said means for raising and lowering the temperature of said polymer cladding material. An advanced modulation principle, so-called serrodyne modulation, can be used to obtain a sensor response of the present interferometer with high sensitivity. Serrodyne signal processing requires a sinusoidal output signal in order to perform Fourier analysis for optical phase determination. The heater yields primarily a square root modulation in response to an applied voltage. Therefore, a modulation voltage optimized such that a sinusoidal optical modulation is obtained, can be encoded in a lookup table and via a digital/analogue converter send to an electronic circuit. Using diodes, the positive and negative voltages are then routed to separate electrical amplifier cicuits which drive the electrical heaters. This way, using a single input modulation signal, derived from a single loopup table, can be used to sequentially drive the heaters of the two thermo-optic modulators of the present interferomter in order to obtain the sinusoidal optical response, thereby compensating for the non-linear voltage dependent behavior of the thermo-optical effect. Also, the influence of temperature on the resistance of the heaters can be compensated for by a correct design of the lookup table. Instead of two heater elements also one heater element can be provided.

In a further preferred embodiment of an integrated optical waveguide interferometer according to the invention a polarization metal strip is used as said means for raising and lowering the temperature of said polymer cladding material. The present interferometer operates well with one of the two possible light polarization states (TE and TM) only. The optical fiber that inputs the interferometer delivers both polarizations. Therefore a polarization stripper is preferred. This might be done by selective absorption of one of the polarizations (TM) in the Si substrate material in the transport section of the interferometer. This yields an attenuation of <10 dB/cm. A much higher value (shorter stripper) can be obtained by selective TM mode absorption in a metal layer. In the interferometer this can be the metal layer of the heater. The heater and stripper funtionality can be decoupled by applying multilayer metal structures (e.g. Cr/Au with Cr for stripping and Au for heating).

The present invention also relates to the use of an integrated optical waveguide interferometer according to the invention in a dipstick.

The invention will further be elucidated with the help of a drawing relating to a preferred embodiment of an integrated optical interferometer in accordance with the invention, wherein FIG. 1 is a schematic layout of a standard integrated optical interferometer of the Mach-Zehnder type;

Figure 3:
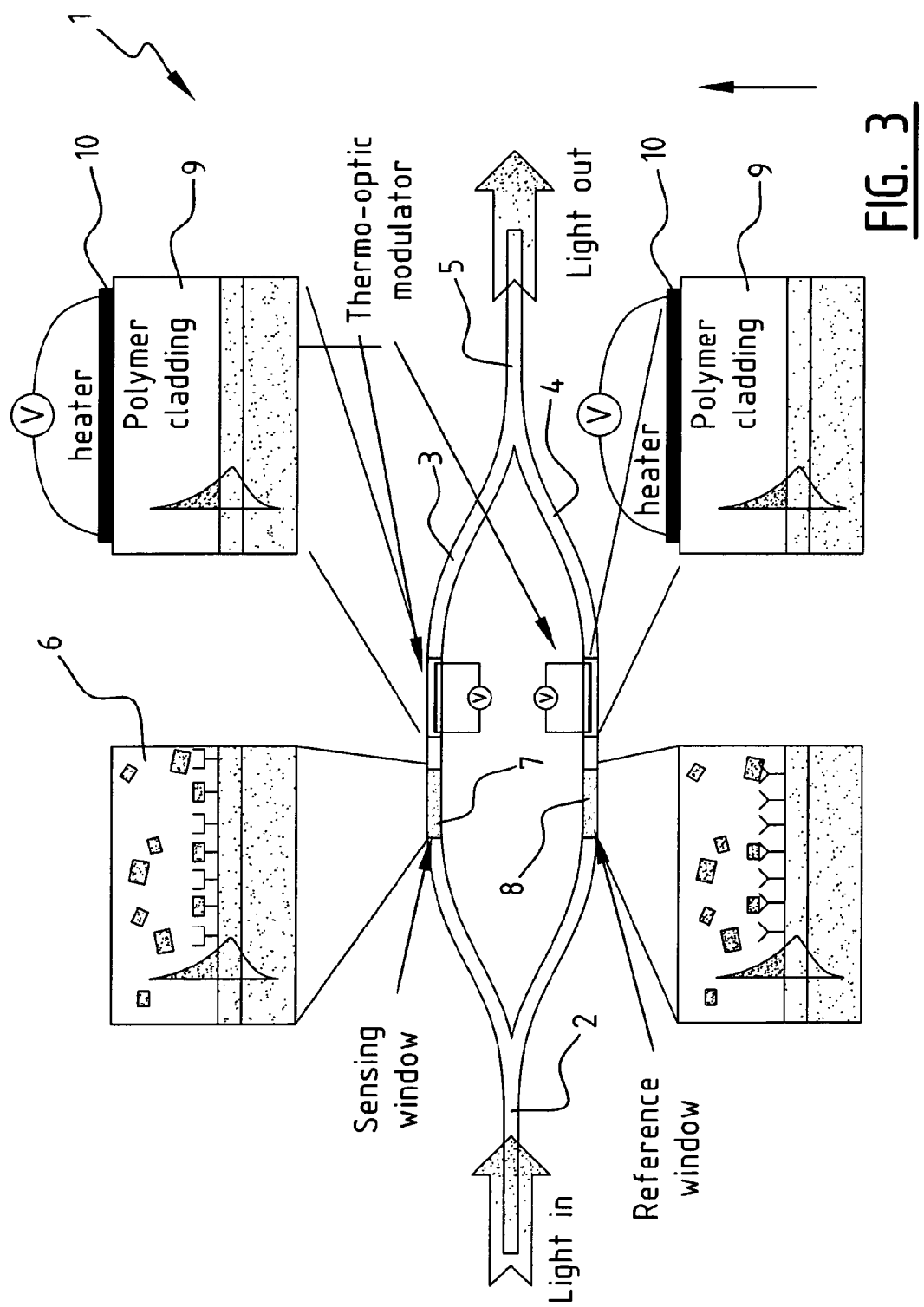
FIG. 3 is a schematic layout of the interferometer of FIG. 2, but now adapted in accordance with the invention.

FIG. 4 relates to a specific use of the interferometer of FIG. 3, that is as a dipstick.

Figure 1:
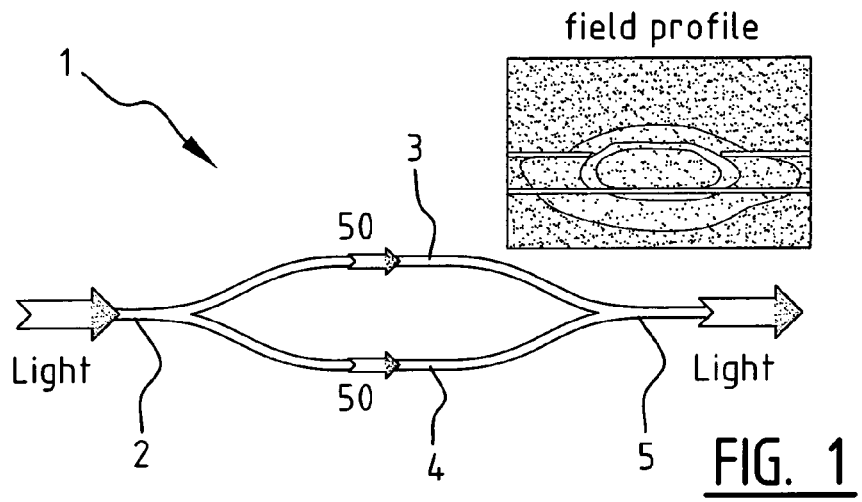

The interferometer 1 of FIG. 1 consists of an input channel waveguide 2 that splits up in two identical branches 3, 4. After a well-defined length, these two branches 3, 4 are combined again to form the output waveguide 5. Light that enters the input waveguide 2 splits equally over the two branches 3, 4 and combines again at the output waveguide 5. The cross-section of the optical waveguide channel of the interferometer 1 consists of a high refractive index core layer with a ridge profile that is sandwiched between low refractive index buffer layers. In case of buried waveguides, the optical field is completely contained in the core and buffer layers and the propagation of light is not affected by environmental disturbances.

Figure 2:
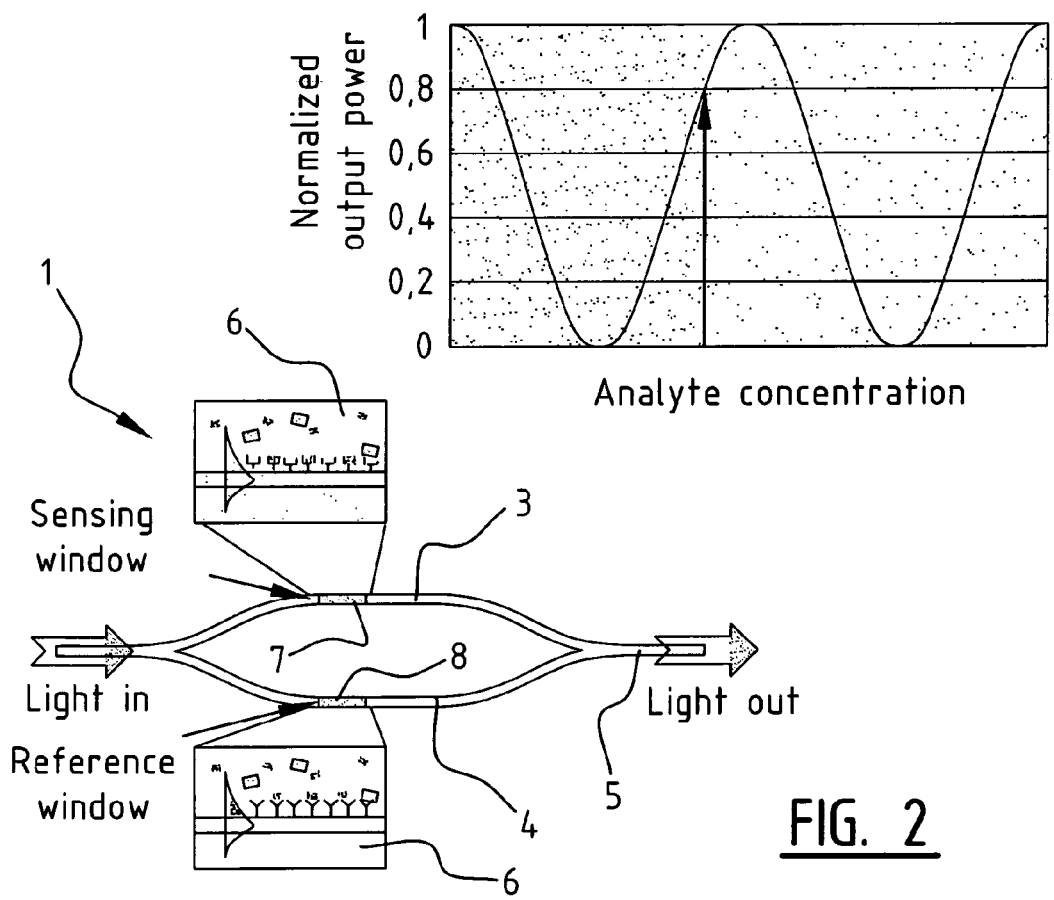
FIG. 2 is a schematic layout of the functioning of the standard interferometer of FIG. 1 for evanescent sensing of chemical and/or physical quantities.

With reference to FIG. 2, by using etching techniques, a top cladding 6 is locally removed above the channel waveguides at well-defined positions in both branches 3, 4 of the interferometer 1. In these so-called windows 7, 8, the evanescent field of the light that travels through the under-laying channel waveguides, extents into the environment above the interferometer 1 and becomes susceptible to environmental changes. An interface layer that binds specifically with analyte molecules of interest is provided on the surface of the sensing window 7. To keep the interferometer 1 balanced, the reference window 8 is provided with an interface layer that shows no specific binding. When sample material is flown over both sensing and reference window 7, 8, specific binding of analyte molecules to the interface layer in the sensing window 7 is probed by the evanescent field of the light travelling through the sensing branch 3. This causes a change of the propagation speed of the light, resulting in a phase difference between light coming from the sensing branch 3 and the reference branch 4 at the output waveguide 5. The induced phase difference is proportional to the amount of analyte molecules binding to the interface layer and results in a periodic change of the light intensity in the output waveguide 5.

With reference to FIG. 3, by using etching techniques, a top cladding 6 is locally removed above the waveguide channels at well-defined positions in both branches 3,4. These so-called modulation sections are filled with a high refractive index polymer cladding material 9, that is having an index of refraction been 1.46 and 2.5 that varies with temperature. Onto this polymer cladding material 9, a metallic heaterstrip 10 is disposed to change the polymer refractive index upon heating or cooling. This will change the phase of light flowing through the channel to effect modulation of the light in the interferometer. Using an advanced modulation principle (serrodyne modulation) in combination with the thermo-optic active section in the interferometer 1 and dedicated electronics, the output intensity of the interferometer 1 is transformed into a sensor response signal that is equal to the induced phase difference caused by specific binding of analyte molecules to the interface layer in the sensing window 7.

Figure 4A:
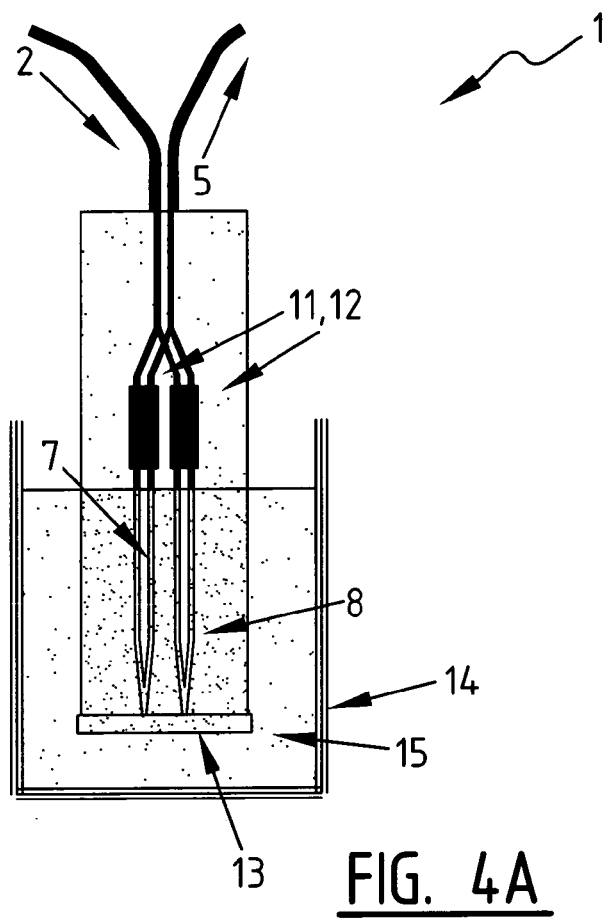
Figure 4B:
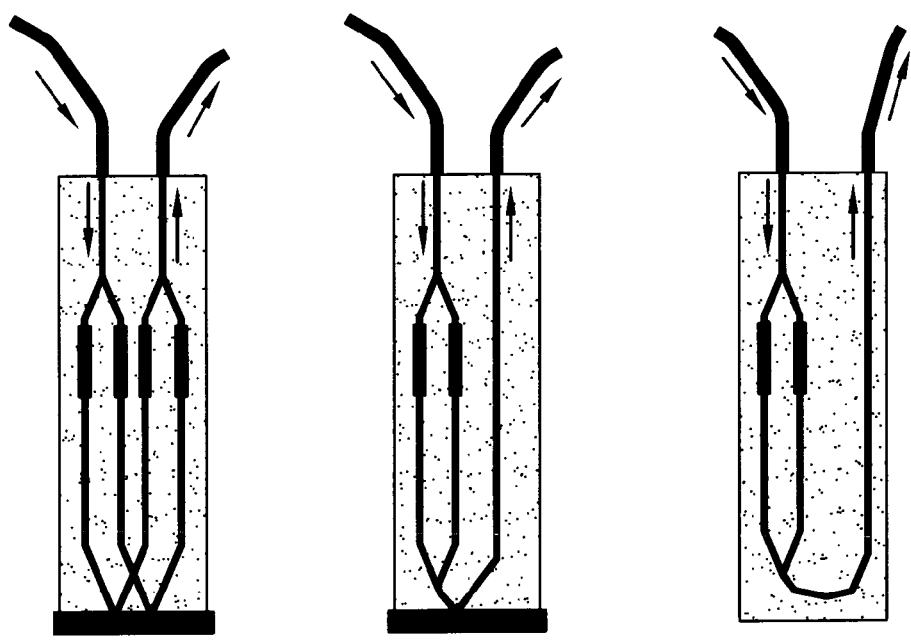

FIG. 4a shows a specific use of the present interferometer shown in FIG. 3, namely as a dipstick 1 with thermo-optic modulators 11, 12. This interferometer is based on a Mach-Zehnder interferometer having waveguides that are routed back to the input edge of the chip by using a folding mirror 13 or a waveguide bend. As a result, the present interferometer is very compact and is used, as shown, in a dipstick application. In other words, the sensor end may be dipped into a container 14 filled with a (small) quantity of a substance 15 to be analyzed. FIG. 4b shows alternative dipstick structures.

The invention claimed is:

1. Integrated optical waveguide interferometer sensor comprising a substrate carrying a waveguide layer structure, the integrated optical waveguide interferometer sensor configured for sensing of at least one of chemical or physical quantities, the waveguide layer structure comprising:

a sensing branch comprising a first waveguide core layer sandwiched between two first cladding layers formed by a first lower cladding layer and a first upper cladding layer, of a lower refractive index than the first waveguide core layer;

a reference branch comprising a second waveguide core layer sandwiched between two second claddings layers formed by a second lower cladding layer and a second upper cladding layer, of a lower refractive index than the second waveguide core layer;

a splitter and a combiner for optically coupling said first and second waveguide core layers at first and second junctions, respectively;

a modulation section of a polymer cladding material included in at least one of the first upper cladding layer or the second upper cladding layer, wherein the polymer cladding material is applied within a window between the first and second junctions, the window comprising a region formed by the at least one of the first upper cladding layer or the second upper cladding layer originally in the region being locally removed, wherein the polymer cladding has a higher refractive index than the first or second lower cladding layer such that an evanescent field of light traveling through the sensing branch or the reference branch is pulled into the polymer cladding material, said polymer cladding material having an index of refraction that varies with temperature;

means for raising and lowering the temperature of said polymer cladding material, such that the modulation section thereby is configured to change the phase of radiation propagating through at least one of said first and second waveguide core layers; and a sensing window included in the sensing branch, wherein the sensing window is configured such that, in the sensing window, the evanescent field of light traveling through the sensing branch extents into an environment above the sensor and is susceptible to an environmental change.

2. Integrated optical waveguide interferometer sensor according to claim 1, wherein said interferometer in said modulation section satisfies the equations:

$$n_c > n_s \quad (1)$$

$$V = 2\pi(h/\lambda)(n_f^2 - n_c^2)^{1/2} \quad (2)$$

$$r = (n_f^2 - n_s^2)/(n_f^2 - n_c^2) \quad (3)$$

with $n_c$ being the refractive index of the first upper cladding layer and/or the second upper cladding layer;

$n_s$ being the refractive index of the first lower cladding layer and/or the second lower cladding layer;

$n_f$ being the refractive index of the first core layer and/or the second core layer;

h being the thickness of the first core layer and/or the second core layer;

λ being the optical wavelength; and

V varying between 0.1 and 4 for r>1.1.

3. Integrated optical waveguide interferometer sensor according to claim 1, wherein said polymer cladding material is at least substantially made from a material selected from the group consisting of poly pentabromophenyl methacrylate, poly pentabromophenyl acrylate, poly pentabromobenzyl methacrylate, poly pentabromobenzyl acrylate, poly 2,4,6-tribromophenyl methacrylate, polyvinylphenyl sulfide, poly 1-napthyl methacrylate, poly 2-vinylthiophene, poly 2,6-dichlorostyrene, poly N-vinylphthalamide, and poly 2-chlorostyrene en poly pentachlorophenyl methacrylate.

4. Integrated optical waveguide interferometer sensor according to claim 3, wherein high refractive index particles have been added to the material of said polymer cladding material in order to increase the index of refraction thereof.

5. Integrated optical waveguide interferometer sensor according to claim 1, wherein said polymer cladding material is at least substantially made from a material selected from the group consisting of a polymer based on aromatic benzene rings and a polymer based on fused aromatic rings.

6. Integrated optical waveguide interferometer sensor according to claim 1, wherein said means for raising and lowering the temperature of said polymer cladding material comprises at least one of a heater or a cooler adjacent to the section of said polymer cladding material.

7. Integrated optical waveguide interferometer sensor according to claim 1, wherein at least one of said first waveguide core layer or said second waveguide core layer is provided with a profile in the form of a ridge.

8. Integrated optical waveguide interferometer sensor according to claim 1, wherein the refractive index of at least one of said first waveguide core layer and said second waveguide core layer is selected in the range between 1.5 and 2.5.

9. Integrated optical waveguide interferometer sensor according to claim 1, wherein at least one of said first waveguide core layer or said second waveguide core layer is at least substantially made from a material selected from the group consisting of $Si_3N_4$, $TiO_2$, $Ta_2O_3$, $ZrO_2$, $Al_2O_3$, $Y_2O_3$ and $Nb_2O_5$.

10. Integrated optical waveguide interferometer sensor according to claim 1, wherein at least one of said first lower cladding layer or said second lower cladding layer is at least substantially made from thermally grown or chemical vapor deposited (CVD) silica, silica containing multicomponent glasses, fluoride glasses, silicon containing organic polymers or silica containing hybrid organic-inorganic polymers or fluorine containing organic polymers or fluorine containing hybrid organic-inorganic polymers.

11. Integrated optical waveguide interferometer sensor according to claim 1, wherein said means for raising and lowering the temperature of said polymer cladding material comprises a metal strip.

12. Integrated optical waveguide interferometer sensor according to claim 1, wherein a foam is applied on said means for raising and lowering the temperature of said polymer cladding material.

13. Integrated optical waveguide interferometer sensor according to claim 1, wherein a coverplate is applied on said means for raising and lowering the temperature of said polymer cladding material, and wherein an airgap is maintained between said coverplate and said means for raising and lowering the temperature of said polymer cladding material.

14. Integrated optical waveguide interferometer sensor according to claim 1, wherein means are provided for electrical modulation of a signal of said means for raising and lowering the temperature of said polymer cladding material.

15. Integrated optical waveguide interferometer sensor according to claim 1, wherein the integrated optical waveguide interferometer sensor is attached to a dipstick, wherein the dipstick comprises an optical chip, and wherein an input fiber of the integrated optical waveguide interferometer sensor and an output fiber of the integrated optical waveguide interferometer sensor are located at a same endface of the optical chip.

16. Integrated optical waveguide interferometer sensor according to claim 1, wherein the index of refraction of said polymer cladding material is between 1.46 and 2.5.

17. Integrated optical waveguide interferometer sensor according to claim 1, wherein the sensing window comprises an interface layer above the first waveguide core layer, wherein the interface layer is configured to bind with given analyte molecules, wherein the sensing window is configured such that the evanescent field of light traveling through the sensing branch probes specific binding of the given analyte molecules to the interface layer.

18. Integrated optical waveguide interferometer sensor according to claim 17, further comprising a reference window included in the reference branch, the reference window comprising a second interface layer above the second waveguide core layer, wherein the second interface layer is configured to avoid binding with the given analyte molecules, and wherein the sensing branch and reference branch are branches in a single interferometer that (i) splits light from a single source into a first portion that travels through the reference branch and a second portion that travels through the sensing branch and (ii) combines the first and second portions at an output end of the single interferometer.

19. Integrated optical waveguide interferometer sensor according to claim 18, wherein the interface layer is formed in a sensing region in which the first upper cladding layer originally in the sensing region is locally removed, and wherein the second interface layer is formed in a reference region in which the second upper cladding layer originally in the reference region is locally removed.

20. Integrated optical waveguide interferometer sensor according to claim 17, wherein the specific binding causes a change in a propagation speed of the light traveling through the sensing branch, the change in the propagation speed resulting in a phase difference between light coming from the sensing branch and light coming from the reference branch, wherein the phase difference is proportional to an amount of the given analyte molecules binding to the interface layer.

21. Integrated optical waveguide interferometer sensor according to claim 17, wherein an in-time induced periodic change of the temperature of the upper polymer cladding in the modulation section induces an in-time periodic phase difference between light coming from the sensing branch and light coming from the reference branch, wherein the phase difference results in an in-time periodic change of an output intensity of the interferometer sensor.

22. Integrated optical waveguide interferometer sensor according to claim 17, wherein the interferometer sensor is configured to transform an output of the interferometer sensor into a sensor response signal that is equal to an induced phase difference caused by a specific binding of the given analyte molecules to the interface layer in the sensing window.

23. Integrated optical waveguide interferometer sensor according to claim 22, wherein the interferometer sensor is configured to apply a modulation principle in combination with the modulation section to transform the output into the sensor response signal.

24. Integrated optical waveguide interferometer sensor according to claim 17, further comprising a reference window included in the reference branch, wherein the sensing branch and reference branch are branches in a single interferometer that (i) splits light from a single source into a first portion that travels through the reference branch and a second portion that travels through the sensing branch and (ii) combines the first and second portions at an output end of the single interferometer.

25. Integrated optical waveguide interferometer sensor according to claim 1, wherein the sensing window comprises a sensing region formed by the first upper cladding layer originally in the sensing region being locally removed, and wherein the sensing branch and reference branch are branches in a single interferometer.

26. Integrated optical waveguide interferometer sensor comprising a substrate carrying a waveguide layer structure, the integrated optical waveguide interferometer sensor configured for sensing of at least one of chemical or physical quantities, the waveguide layer structure comprising:
   a sensing branch comprising a first waveguide core layer sandwiched between two first cladding layers formed by a first lower cladding layer and a first upper cladding layer, of a lower refractive index than the first waveguide core layer;
   a reference branch comprising a second waveguide core layer sandwiched between two second claddings layers formed by a second lower cladding layer and a second upper cladding layer, of a lower refractive index than the second waveguide core layer;
   a splitter and a combiner for optically coupling said first and second waveguide core layers at first and second junctions, respectively;
   a modulation section of a polymer cladding material included in at least one of the first upper cladding layer or the second upper cladding layer, wherein the polymer cladding material is applied within a window between the first and second junctions, the window comprising a region formed by the at least one of the first upper cladding layer or the second upper cladding layer originally in the region being locally removed, wherein the polymer cladding has a higher refractive index than the first or second lower cladding layer such that an evanescent field of light traveling through the sensing branch or the reference branch is pulled into the polymer cladding material, said polymer cladding material having an index of refraction between 1.46 and 2.5 that varies with temperature;
   a heater configured to raise the temperature of said polymer cladding material, such that the modulation section thereby is configured to change the phase of radiation propagating through at least one of said first and second waveguide core layers; and
   a sensing window included in the sensing branch, wherein the sensing window is configured such that, in the sensing window, the evanescent field of light traveling through the sensing branch extents into an external environment and is susceptible to an environmental change.

27. Integrated optical waveguide interferometer sensor according to claim 26, further comprising a cooler configured to lower the temperature of said polymer cladding material.

28. Integrated optical waveguide interferometer sensor comprising a substrate carrying a waveguide layer structure, the integrated optical waveguide interferometer sensor configured for sensing of at least one of chemical or physical quantities, the waveguide layer structure comprising:
   a sensing branch comprising a first waveguide core layer sandwiched between two first cladding layers formed by a first lower cladding layer and a first upper cladding layer, of a lower refractive index than the first waveguide core layer;
   a reference branch comprising a second waveguide core layer sandwiched between two second claddings layers formed by a second lower cladding layer and a second upper cladding layer, of a lower refractive index than the second waveguide core layer;
   a splitter and a combiner for optically coupling said first and second waveguide core layers at first and second junctions, respectively;
   a sensing window included in the sensing branch, the sensing window comprising an interface layer above the first waveguide core layer, wherein the interface layer is configured to bind with given analyte molecules;
   a reference window included in the reference branch, the reference window comprising a second interface layer above the second waveguide core layer, wherein the second interface layer is configured to avoid binding with the given analyte molecules;
   a modulation section of a polymer cladding material included in at least one of the first upper cladding layer or the second upper cladding layer, wherein the polymer cladding material is applied within a window between the first and second junctions, the window comprising a region formed by the at least one of the first upper cladding layer or the second upper cladding layer originally in the region being locally removed, wherein the polymer cladding has a higher refractive index than the first or second lower cladding layer such that an evanescent field of light traveling through the sensing branch or the reference branch is pulled into the polymer cladding material, said polymer cladding material having an index of refraction that varies with temperature; and
   means for raising and lowering the temperature of said polymer cladding material, such that the modulation section thereby is configured to change the phase of radiation propagating through at least one of said first and second waveguide core layers.

* * * * *